United States Patent [19]

Hironaka et al.

[11] Patent Number: 4,792,644
[45] Date of Patent: Dec. 20, 1988

[54] PREPARATION OF HALOGENATED BENZENE DERIVATIVES

[75] Inventors: Toshio Hironaka; Kazuhiko Sekizawa; Yukihiro Tsutsumi, all of Yamaguchi, Japan

[73] Assignee: Tosoh Corporation, Yamaguchi, Japan

[21] Appl. No.: 63,385

[22] Filed: Jun. 18, 1987

[30] Foreign Application Priority Data

Jun. 18, 1986 [JP] Japan ............................... 61-140140

[51] Int. Cl.$^4$ ...................... C07C 17/10; C07C 25/00
[52] U.S. Cl. .................................. 570/208; 570/206; 570/207
[58] Field of Search .................. 570/206, 208, 207

[56] References Cited

FOREIGN PATENT DOCUMENTS 118851  9/1984  European Pat. Off. .......... 570/208

Primary Examiner—Werren B. Lone
Attorney, Agent, or Firm—Sughrue, Mion, Zinn, Macpeak, and Seas

[57] ABSTRACT

In the liquid phase chlorination of benzene derivatives including benzene per se in the presence of a zeolite possessing the main pores having the opening formed of a 12-membered oxygen ring; para-substituted chlorinated benzene derivatives are preferentially obtained by adding a small quantity of a quaternary ammonium salt or salts to the reaction mixture.

13 Claims, No Drawings

PREPARATION OF HALOGENATED BENZENE DERIVATIVES

This invention relates to a process for preparing halogenated benzene derivatives by halogenation of benzene derivatives in the liquid phase. In particular, the invention relates to such a process in which a zeolite possessing the main pores having the opening formed of a 12-membered oxygen ring is used as a catalyst and a quaternary ammonium salt is present in the reaction system so as to give preferentially para-substituted halogenated benzene derivative products.

Halogenated benzene derivatives are industrially important intermediate feedstocks which have various applications in the field of organic synthesis chemistry, for example in the production of various chemical products, such as pharmaceuticals and agricultural chemicals. Generally, the derivatives have been prepared by chlorinating benzene derivatives in the liquid phase using a catalyst comprising a Lewis acid, such as ferric chloride or antimony chloride. For example, dichlorobenzene (hereinafter referred to as DCB) may be prepared by blowing gaseous chlorine either into benzene or monochlorobenzene (hereinafter referred to as MCB) in the presence of a ferric chloride catalyst.

The liquid phase chlorination of a mono-substituted benzene derivative to produce the corresponding di-substituted derivatives will give a product comprising three isomers, i.e. 1,2-di-substituted (ortho-), 1,3-di-substituted (meta-) and 1,4-di-substituted (para-) isomers. It is well known that the relative proportions of these product isomers are largely governed by certain factors such as the substituent originally present in the starting mono-substituted derivative and the nature of the catalyst used in the chlorination. For example, where MCB is chlorinated to DCB in the liquid phase in the presence of ferric chloride, the approximate relative proportions of the three product DCB isomers will be:

ortho-dichlorobenzene: 30–40%
meta-dichlorobenzene: 0–5%
para-dichlorobenzene: 60–70%

Of the three substituted halogenated isomers prepared from various starting benzene derivatives, the para-substituted halogenated benzene derivatives are generally most important and are needed in large quantities in the chemical industry. Accordingly, a number of processes for preparing preferentially para-substituted halogenated benzene derivatives have been proposed.

As an example of these prior art processes, a process has been proposed for producing preferentially para-substituted halogenated benzene derivatives in which a benzene derivative is halogenated using zeolites as a catalyst. For example, in "Journal of Catalysts" 60, 110 (1979), the use of zeolites as catalysts for brominating halogenated benzenes is reported. In this reference, various ion-exchanged zeolites, i.e. of the X and Y types, are employed to preferentially give para-substituted bromobenzenes.

In "Tetrahedron Letters" 21, 3809 (1980), a process for chlorinating benzene using a catalyst comprising ZSM-5, ZSM-11, mordenite, zeolite L or zeolite Y is reported. It is said that particularly where zeolite L is employed, paradichlorobenzene (hereinafter referred to as PDCB) is yielded at a significantly high selectivity. Further, halogenation processes in which benzene or alkyl benzenes are halogenated in the presence of a catalyst comprising zeolite L or Y are disclosed, for example, in Japanese Patent Public Disclosures (KOKAIs) Nos. 59-130227, 59-144722 and 59-163329. It is also reported that where a zeolite which has been treated with a lower acylating agent or an aliphatic carboxylic acid or a salt therof is employed as a catalyst in halogenation processes, for example of toluene, an improved selectivity to para-substituted halogenated benzene derivatives is achieved. Further, "Chemistry Letters", page 2007 (1984) reports that in bromination of aniline using zeolite A carrying bromine adsorbed thereonto, the bromination activity and the selectivity to para-bromoaniline are improved, when pyridine or 2,6-lutidine is added to the reaction system.

From the prior art, it is apparent that, in the liquid phase halogenation of benzene derivatives, where zeolites are used as a catalyst, the corresponding para-substituted halogenated benzene derivatives are produced more preferentially than the case where a conventional catalyst comprising a Lewis acid such as ferric chloride is used.

However, the yield of the desirable product para-substituted halogenated benzene derivatives achieved by the prior art processes using these zeolite catalysts has not been completely satisfactory in practice. Therefore, there has been a great need for a process to be developed in which para-substituted halogenated benzene derivatives are formed in yields which show further improvement over the level of the prior art.

Under these circumstances, we have made intensive efforts to fully investigate and study the halogenation of benzene derivatives in the liquid, phase using in particular zeolite catalysts, so as to develop a process by which para-substituted halogenated benzene derivatives may be preferentially prepared.

As a result, we have surprisingly found that, in a halogenation process using a catalyst comprising a zeolite possessing the main pores which have the opening formed of a 12-membered oxygen ring, when a quaternary ammonium salt is present in the reaction system, the selectivity to halogenation at the para-position is significantly improved without substantially changing the catalytic activity.

Thus, the present invention provides a process for preparing halogenated benzene derivatives in which a benzene derivative is subjected to halogenation in the liquid phase in the presence of a catalyst comprising a zeolite possessing the main pores which have the opening formed of a 12-membered oxygen ring; characterized in that at least one quaternary ammonium salt is present in the reaction system.

The invention will be described in more detail below.

In the present process, certain tYpes of zeolites may be used as a catalyst. Generally, "zeolites" are the aliases of crystalline aluminosilicates. Zeolites are constructed by $SiO_4$ and $AlO_4$ tetrahedra. Zeolites have been classified into a plurality of types according to the manner in which these tetrahedra form links with each other. The zeolites which ma be used as a catalyst in the present process are those which possess the main pores having the opening formed of a 12-membered oxygen ring. As examples, faujasite-type zeolites, zeolite L, mordenite, cancrinite, gmelinite, offretite, etc. may be mentioned. Faujasite-type zeolites and zeolite L are preferred.

Although, faujasite-type zeolites occur in nature, they may be synthesized by known methods. The synthetic faujasite-type zeolites are well known a zeolite X and zeolite Y. In the present process, synthetic faujasite-type zeolites, in particular zeolite Y, which are completely free of contaminants and highly crystalline are preferably employed.

Since faujasite-type zeolites have a characteristic crystal structure, they may be readily distinguished from other zeolites by employing powder X-ray diffractiometry.

The chemical composition of faujasite-type zeolites may be represented by the following formula as expressed in terms of the molar ratio of the oxides:

a $M_{2/n}O \cdot Al_2O_3 \cdot b\ SiO_2$ (wherein a=1.0±0.3, b ranges from 2 to 8, and n is the valence of cation M).

Zeolite L is a synthetic zeolite which may be synthesized by known methods. Zeolite L also has a characteristic crystal structure and is distinguishable from other zeolites by employing powder X-ray diffractiometry.

The typical composition of zeolite L is represented by the following formula as expressed in terms of the molar ratio of the oxides:

a $M_{2/n}O \cdot Al_2O_3 \cdot b\ SiO_2$ (wherein a=1.0±0.3, b ranges from 4 to 8, and n is the valence of cation M).

Zeolites, such as mordenite, oancrinite, gmelinite and offretite may also be synthesized by known methods. These are respectively distinguishable from other zeolites by utilizing X-ray diffractiometry.

Generally, the synthetic zeolites, in their assynthesized states, contain cations such as sodium cations and potassium cations. For use in the present process, the kind of the cations contained in the zeolites does not appear to be critical. Therefore, zeolites containing cations, such as sodium or potassium cations, which have been introduced during synthesis may be used in that state as a catalyst in the present process. However, if necessary, the original cations may be exchanged with any other suitable cations before the synthetic zeolites are used in the present process. This may be achieved merely by subjecting the original cation-containing zeolite to ion-exchange treatment in the known manner with an aqueous solution containing the cations to be introduced in place of the original cations.

In the present process, the ion-exchanged zeolites may be used in that state as a catalyst. However, it is preferable for the ion-exchanged zeolites to be further modified with a suitable metal salt before they are used in the present process. The modification of zeolites with the metal salt may be achieved by known methods, for example the method disclosed in Japanese Patent Public Disclosure (KOKAI) No. 61-189236. In the known methods, the zeolite materials are brought into intimate contact with an appropriate metal salt, for example by impregnation, mixing or a milling technique. For the purpose of the present invention, although the method which may be employed for modifying the zeolite material with a metal salt is not limited to any specific one, a conventional impregnation method in which a metal salt is dissolved in a suitable solvent, e.g. water, and a zeolite material is impregnated with the resulting solution is conveniently used, because by such a method not only can the exterior surfaces of the zeolite material be intimately impregnated with the salt, but the interior surfaces within the pores thereof can be intimately impregnated too, and the impregnation procedure is simple.

For the modification purpose, any suitable metal salt may be selected from, for example, halides, carbonates and sulfates etc. of alkali, alkaline earth, rare earth metals etc. Particular examples thereof include chlorides of sodium, potassium, strontium, barium and lanthanum; carbonates of sodium, potassium, strontium and barium; and sulfates of sodium, potassium, strontium and barium.

The amount of metal salt used for the modification ranges from about 0.1% to about 90%, preferably from about 10% to about 80%, by weight on the basis of the weight of catalyst zeolite. In the present process, the zeolite catalyst may be used in any physical form or shape. The zeolite material may be formed into a molded catalyst by the conventional techniques or may be used in the form of powder. Thus, the catalyst may be shaped, for example, by extrusion, pelletizing, spray-dry-granulation or other conventional techniques. To improve or modify the physical properties, for example the mechanical strength, of the catalyst, one or more additive materials such as a binder or a shaping aid which are substantially inert under the process conditions of the invention may be added to the zeolite material before shaping or forming. For example, silica, clays, graphite, stearic acid, starch or polyvinyl alcohol may be added in an amount of about 0–80%, preferably about 2–30%, by weight.

The thus prepared catalyst, after drying if necessary, is calcined for a period of from about 10 minutes to about 24 hours in a stream of air or an inert gas, such as nitrogen or helium. The calcination temperature may range from about 200° C. to about 900° C. and is preferably within the range of about 300°–850° C. The thus calcined catalyst may be used in the liquid phase halogenation according to the invention.

In the present process, the liquid phase halogenation of benzene derivatives is effected in the presence of a quaternary ammonium salt in the liquid phase reaction system. The term "quaternary ammonium salt" used herein is intended to mean a compound consisting of (a) a quaternary ammonium ion including a tetravalent nitrogen atom free of nitrogen-hydrogen bond and (b) an anion. The quaternary ammonium ion may be represented by either of the following general formulae (I), (II) and (III):

(I)

wherein $R_1$, $R_2$, $R_3$ and $R_4$, which may be the same or different, each represent a hydrocarbonaceous group having from 1 to 20 carbon atoms and optionally containing carbon-to-carbon unsaturation or an aryl, hydroxyl, halogeno, ester or carboxyl group or groups;

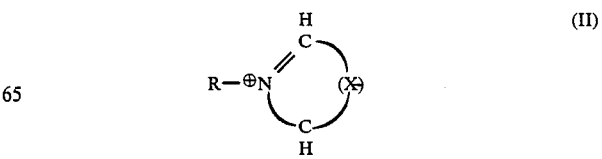
(II)

wherein R represents a hydrocarbonaceous group having from 1 to 20 carbon atoms and which contains optionally carbon-to-carbon unsaturation or an aryl, hydroxyl, halogeno, ester or carboxyl group or groups, and X represents a $C_1$-$C_{11}$ hydrocarbon chain containing from 0 to 3 nitrogen atoms; and

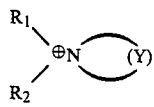 (III)

wherein $R_1$ and $R_2$, which may be the same or different, each represent a hydrocarbonaceous group having from 1 to 20 carbon atoms and optionally containing carbon-to-carbon unsaturation or an aryl, hydroxyl, halogeno, ester or carboxyl group or groups, and Y represents a $C_3$-$C_{13}$ hydrocarbon chain containing from 0 to 3 nitrogen atoms.

Examples of the quaternary ammonium ions represented by the general formula (I) include alkyl-containing quaternary ammonium ions, such as tetramethyl- and tri-n-propyl-ethyl-ammonium ions; aryl and alkyl-containing quaternary ammonium ions, such as phenyl-trimethyl ammonium ion; aralkyl and alkyl-containing quaternary ammonium ions, such as benzyl trimethyl ammonium ion; and other quaternary ammonium ions containing a hydrocarbonaceous group substituted with hydroxy, halogen, ester group etc., such as 2-hydroxyethyl trimethyl-, 2-chloroethyl trimethyl- and 2-acetoxyethyl trimethyl-ammonium ions. Preferred are tetramethyl-, tetraethyl-, tetra-n-propyl-, tetra-n-butyl-, phenyl trimethyl- and benzyl trimethyl-ammonium ions.

Examples of the quaternary ammonium ions represented by the general formula (II) include pyridinium ions, such as methyl- and lauryl-pyridinium ions; quinolinium ions, such as methyl quinolinium ion; and imidazolinium ions, such as 1,3-dimethyl imidazolinium ion. Preferred are methyl-, ethyl and lauryl-pyridinium and methyl and ethyl quinolinium Examples of the quaternary ammonium ions represented by the general formula (III) include pyrrolidinium ions, such as N,N-dimethyl pyrrolidinium ion; piperidinium ion, such as N,N-dimethyl piperidinium ion; and piperazinium ions, such as N,N,N',N'-teramethyl piperazinium.

The anion which is bound to the quaternary ammonium ion to form the salt is not restricted to any specific one. Examples of suitable anions include halide ions, such as fluoride, chloride, bromide and iodide ions; hexafluorophosphate ion; perchlorate ion; and tetrafluoroborate ion. Halide ions, such as chloride, bromide and iodide ions are preferred.

In the present process, one of the specified quaternary ammonium salts may be employed singly. Alternatively, any appropriate combination of two or more salts may be used.

The quaternary ammonium salt or salts should be present in the reaction system in which the liquid phase halogenation is effected. The salt may be introduced into the reaction system in any suitable manner. For example, the quaternary ammonium salt may be introduced into the reaction system separately from the feedstock and the catalyst, or may be adsorbed onto or supported on the catalyst zeolite prior to introduction into the reaction system.

Because the amount of the quaternary ammonium salt that should be present effectively in the reaction system will depend upon various factors, for example the kind of the particular salt selected from the wide range of salts available, the manner in which the salt is introduced into the reaction system, the kind of the zeolite used therewith, etc. ----, it is difficult to specify the amount unconditionally on a common basis. However, it has been found that the amount may be conveniently specified on the basis of the weight of the nitrogen atoms contained in the particular quaternary ammonium salt. Thus, generally, the amount of the quaternary ammonium salt which may be used in the present process ranges from $1 \times 10^{-5}$ gr./gr. zeolite to 0.1 gr./gr. zeolite, and preferably from $1 \times 10^{-4}$ gr./gr. zeolite to $5 \times 10^{-2}$ grs./gr. zeolite, as expressed in terms of the weight of the nitrogen atoms per unit weight of the zeolite. If the amount is less than $1 \times 10^{-5}$ gr./gr. zeolite, the effect of improving the selectivity to the para-substituted halogenated benzene derivative is unacceptably low. Where the amount exceeds 0.1 gr./gr. zeolite, the catalytic activity of zeolite may then be adversely affected.

Herein, the term "benzene derivative" is intended to include benzene per se and benzene compounds in which a hydrogen atom is substituted with a substituted such as a halogen or alkyl group having 1 to 10 carbon atoms, for example halogenated benzenes and alkyl benzenes. Particular examples thereof include benzene, monofluorobenzene, monochlorobenzene (MCB), monobromobenzene, monoiodobenzene, toluene and ethylbenzene.

The halogenating agents which may be used in the present process are elementary halogens, for example, chlorine, bromine and iodine.

The apparatus used for the present process, the manner in which the process is operated and the conditions under which the process is conducted are not critical, provided that the feedstock benzene derivative can be maintained in the liquid state and brought into contact with the catalyst during the reaction. For example, the apparatus may be of a continuous, batch-wise or semi-batch-wise type. The catalyst may be used, for example in a fixed bed or in a suspended bed.

The halogenation reaction may be carried out in the presence of a solvent, for example carbon tetrachloride, which is inert under the reaction conditions employed. In such a case, the concentration of the benzene derivative is suitably in the range of about 5-99% by weight, preferably in the range of about 20-99% by weight. With a concentration of as low as less than 5% by weight, the accessibility of the feedstock to the catalyst would become markedly reduced, resulting in an unacceptable level of conversion. Where the halogenation agent is continuously supplied to the reaction, the agent may be diluted with an inert gas, such as nitrogen, helium or carbon dioxide, prior to the introduction into the reaction. Where such a diluent gas is used, the concentration of the halogenating agent in the gaseous mixture is suitably in the range of 5-99%, and preferably 20-99%, by volume.

Where the reaction apparatus employed is either of a batch-wise or semi-batch-wise type, the catalyst is generally used essentially as a suspension in the liquid reaction mixture. Suitably the amount of the catalyst per unit volume of the liquid reaction mixture is in the range of about 0.001-1 kg/l, and preferably about 0.005-0.1kg/l. Where the catalyst amount is less than 0.001 kg/l, the burden of duty on the catalyst would become unduly severe, resulting in an unacceptably low level of conversion. On the other hand, even if the amount exceeds 1 kg/l, no further significant advantages would be achieved. The feed rate of the halogenating agent may be expressed in the quantity of the agent fed per unit weight of the catalyst per unit time and may be in the range of from about 1 to about 1500 mols./kg.cat. ·hr., and preferably from about 10 to about 800 mols./kg.cat. ·hr. When the feed rate is less than 1 mol./kg.cat.·hr., an unacceptably low production rate of halogenated benzene derivative would result. On the other hand, if the feed rate exceeds 1500 mols./kg.cat. hr., then the amount of unreacted halogenating agent would increase to an economically unacceptable level.

Where a continuous reaction apparatus is employed, the feed rate of the benzene derivative feedstock may be expressed in the amount of benzene derivative fed per unit weight of the catalyst per unit time and, suitably, is in the range of from about 0.5 to about 300 ls./kg.cat.·hr., and preferably from about 2 to about 100 ls./kg.cat.·hr. The other conditions which may be used in the continuous reaction apparatus are similar to those used in the batch-wise or semi-batch-wise apparatus as above mentioned.

In the present process, any combination of reaction temperature and pressure may be employed, provided that the benzene derivative is maintained in the liquid phase. When a reaction temperature is higher than the boiling point of the benzene derivative, the pressure would be increased to a level sufficient to permit the halogenation to be conducted in the liquid phase. Preferably the reaction temperature is in the range of from about 0° to about 200° C., more preferably about 20°–150° C. When the temperature is below 0° C., a satisfactory reaction rate cannot be achieved. When the temperature is above 200° C. the selectivity to the para-substituted halogenated benzene derivative would become unduly lowered.

According to the present invention, the commercially valuable para-substituted halogenated benzene derivatives can be obtained in a significantly higher yield as compared with that achieved by the conventional processes. Therefore, the present invention provides a very significant improvement in the art.

EXAMPLE

The invention will be further illustrated with reference to the following examples. It will be appreciated that the examples are only for illustrative purposes and that the invention is not to be limited thereby.

The conversion and selectivity data reported in the examples were calculated in accordance with the following equations, respectively:

$$\text{Conversion (\%)} = \frac{\text{(fed benzene derivative (mol))} - \text{(unreacted benzene derivative (mol))}}{\text{fed benzene derivative (mol)}} \times 100$$

$$\text{Selectivity (\%)} = \frac{\text{yield of a particular product (mol)}}{\text{the total of yields of all the products (mol)}} \times 100$$

EXAMPLE 1

Into a 1 liter porcelain beaker, 12.87 grs. of sodium chloride (NaCl) was added and dissolved in 300 mls. of distilled water. The solution was heated to and maintained at 95° C. in a water bath. An Na-Y type zeolite having an $SiO_2/Al_2O_3$ ratio of 5.5 (30 grs.; sold by Toyo Soda Manufacturing Co.) was added to the solution while it was well stirred with a stirrer having glass vanes. The mixture was evaporated to dryness in the water bath, dried in a drier oven at 130° C. for 15 hours and then calcined in a stream of air at 540° C. for 3 hours to give a sodium cation-containing zeolite Y impregnating 30% by weight of NaCl.

The thus obtained NaCl-modified catalyst was used together with a quaternary ammonium salt, benzyl trimethyl ammonium chloride in the liquid phase chlorination of monochlorobenzene (MCB). The reaction was effected in an ordinary semi-batch-wise apparatus comprising a PYREX glass vessel (40 mm inner diameter, 100 mm height) provided with a gas sparger tube and a condenser. Into the reactor vessel, 40 grs. of MCB, and 0.113 grs. of benzyl trimethyl ammonium chloride were charged and 1.43 grs. of the above prepared zeolite was added to form a suspension. In this case, the quantity of the benzyl trimethyl ammonium chloride present per unit weight of the zeolite was $8.5 \times 10^{-3}$ grs /gr. zeolite, as calculated in terms of the weight of the nitrogen atoms.

The reaction mixture was throughly stirred by means of a magnetic stirrer, while a stream of gaseous chlorine (as a 1:1 chlorine/nitrogen mixture) was bubbled therethrough at a feed rate of 30 mls. chlorine/minute. The reaction temperature was adjusted to 100° C. by immersing the reactor vessel in an oil bath. After blowing the chlorine into the reaction mixture for 3 hours, a sample of the reaction mixture was analyzed by gas-chromatography to identify the obtained products.

The results are shown in Table 1 below.

EXAMPLES 2–5

The procedure of the liquid-phase chlorination of MCB as described in Example 1 was repeated with a catalyst of an Na cation-containing Y-type zeolite modified with NaCl through the catalyst preparation procedure as described in Example 1, except that, in the chlorination, 0.093 grs. of tetramethyl ammonium bromide (Example 2), 0.033 grs. of tetra-n-butyl ammonium bromide (Example 3), 0.115 grs. of ethyl quinolinium iodide (Example 4) or 0.104 grs. of phenyl trimethyl ammonium chloride (Example 5) was used as a quaternary ammonium salt in place of the benzyl trimethyl ammonium chloride.

After 3 hours of the chlorine gas blowing, the reaction mixture was analyzed as in Example 1 to give the results shown in Table 1

COMPARATIVE EXAMPLE 1

The procedure of the MCB liquid phase chlorination as described in Example 1 was repeated with a catalyst of an Na cation-containing Y-type zeolite modified with NaCl through the catalyst preparation procedure as described in Example 1, except that the quaternary ammonium salt was omitted from the reaction mixture. After 3 hours of the chlorine gas blowing, the reaction mixture was analyzed as in Example 1 to give the results shown in Table 1.

TABLE 1

| | Quaternary ammonium salts | | Conversion | Selectivities (%) | | |
|---|---|---|---|---|---|---|
| | Compounds | Quantities[1] (grs./gr. zeolite) | of MCB (%) | PDCB | ODCB[2] | Others[3] |
| Examples | | | | | | |
| 1 | Benzyl trimethyl ammonium chloride | $8.5 \times 10^{-3}$ | 63.8 | 90.0 | 8.6 | 1.4 |
| 2 | Tetramethyl ammonium bromide | $8.5 \times 10^{-3}$ | 63.9 | 87.3 | 11.4 | 1.3 |
| 3 | Tetra-n-butyl ammonium bromide | $1.4 \times 10^{-3}$ | 64.3 | 87.4 | 11.2 | 1.4 |
| 4 | Ethyl quinolinium iodide | $5.7 \times 10^{-3}$ | 65.2 | 88.7 | 10.0 | 1.3 |
| 5 | Phenyl trimethyl ammonium chloride | $8.5 \times 10^{-3}$ | 63.5 | 89.2 | 9.5 | 1.3 |
| Comp. Ex. 1 | — | — | 62.6 | 85.2 | 13.6 | 1.2 |

[1]expressed as the weight (grs.) of the nitrogen atoms per unit weight (gr.) of the zeolite
[2]ODCB: ortho-dichlorobenzene
[3]Others: including meta-dichlorobenzene, trichlorobenzene isomers, etc.

EXAMPLE 6

The procedure of the MCB liquid phase chlorination as described in Example 1 was repeated except that as a catalyst, 1.0 gr. of an Na cation-containing zeolite Y (commercially available from Toyo Soda) was employed in place of the NaCl-modified zeolite of Example 1. After 3 hours of the chlorine gas blowing, the reaction mixture was analyzed as in Example 1 to give the results shown in Table 2 below.

COMPARATIVE EXAMPLE 2

The procedure of the MCB liquid phase chlorination of Example 6 was repeated except that the reaction was effected in the absence of benzyl trimethyl ammonium chloride. After 3 hours of the chlorine gas blowing, the reaction mixture was analyzed to give the results shown in Table 2.

TABLE 2

| | Conversion of MCB (%) | Selectivity (%) | | |
|---|---|---|---|---|
| | | PDCB | ODCB[1] | Others[2] |
| Example 6 | 66.4 | 85.7 | 12.7 | 1.6 |
| Comp. Ex. 2 | 63.4 | 79.1 | 19.3 | 2.0 |

[1]ODCB: ortho-dichlorobenzene
[2]Others: including meta-dichlorobenzene and trichlorobenzene isomers

EXAMPLE 7

The procedure of the MCB liquid phase chlorination as described in Example 1 was repeated except that, as a catalyst, 1.0 gr. of a potassium cation-containing zeolite L having an $SiO_2/Al_2O_3$ ratio of 6.2 (commercially available from Toyo Soda) was used in place of the NaCl-modified zeolite of Example 1 and benzyl trimethyl ammonium chloride was used in an amount of 0.020 grs. In this case, the quantity of the benzyl trimethyl ammonium chloride relative to the zeolite corresponds to $1.5-10^{-3}$ grs. nitrogen atoms per gr. of the zeolite. After 3 hours of the chlorine gas blowing, the reaction mixture was analyzed as in Example 1 to give the results shown in Table 3 below.

EXAMPLE 8

The procedure as described in Example 7 was repeated except that, as a quaternary ammonium salt, 0.011 grs. of tetra-n-butyl ammonium bromide was used in place of the benzyl trimethyl ammonium chloride of Example 7. After 3 hours of the chlorine gas blowing, the reaction mixture was analyzed to give the results shown in Table 3 below.

EXAMPLE 9

The procedure as described in Example 8 was repeated except that the potassium ion-containing zeolite L was employed in an amount of 2.0 grs. instead of 1.0 gr. After 3 hours of the chlorine gas blowing, the reaction mixture was analyzed to give the results shown in Table 3 below.

EXAMPLE 10

The procedure as described in Example 7 was repeated except that, as a quaternary ammonium salt, 0.034 grs. of lauryl pyridinium chloride was used in place of the benzyl trimethyl ammonium chloride of Example 7. After 3 hours of the chlorine gas blowing, the reaction mixture was analyzed to give the results shown in Table 3 below.

COMPARATIVE EXAMPLE 3

The procedure of the MCB liquid phase chlorination as described in Example 7 was repeated except that the reaction was effected in the absence of benzyl trimethyl ammonium chloride. After 3 hours of the chlorine gas blowing, the reaction mixture was analyzed to give the results shown in Table 3 below.

TABLE 3

| | Quaternary ammonium salts | | Conversion | Selectivities (%) | | |
|---|---|---|---|---|---|---|
| | Compounds | Quantities[1] (grs./gr. zeolite) | of MCB (%) | PDCB | ODCB[2] | Others[3] |
| Examples | | | | | | |
| 7 | Benzyl trimethyl ammonium chloride | $1.5 \times 10^{-3}$ | 64.4 | 88.4 | 10.8 | 0.8 |
| 8 | Tetra-n-butyl ammonium bromide | $4.8 \times 10^{-4}$ | 58.9 | 93.4 | 6.0 | 0.6 |
| 9 | Tetra-n-butyl ammonium bromide | $2.4 \times 10^{-4}$ | 63.3 | 88.2 | 11.0 | 0.8 |
| 10 | Lauryl pyridinium | $1.7 \times 10^{-3}$ | 59.0 | 88.9 | 9.9 | 1.2 |

TABLE 3-continued

| | Quaternary ammonium salts | | Conversion | Selectivities (%) | | |
|---|---|---|---|---|---|---|
| | Compounds | Quantities[1] (grs./gr. zeolite) | of MCB (%) | PDCB | ODCB[2] | Others[3] |
| | chloride | | | | | |
| Comp. Ex. 3 | — | — | 62.6 | 87.7 | 11.4 | 0.9 |

[1]expressed as the weight of the nitrogen atoms per unit weight of the zeolite
[2]ODCB: ortho-dichlorobenzene
[3]Others: including meta-dichlorobenzene, trichlorobenzene isomers, etc.

COMPARATIVE EXAMPLES 4 AND 5

In accordance with the method disclosed in U.S. Pat. No. 3,790,471, a ZSM-5 zeolite possessing the main pores having the opening formed of a 10-membered oxygen ring was synthesized. The resulting product was identified by means of powder X-ray diffractory using copper Kα doublet. The ZSM-5 zeolite was calcined in a stream of air at 540° C. The calcined material was subjected to ion-exchange treatment with an aqueous sodium chloride so as to give an Na ion-exchanged ZSM-5 zeolite having the following composition as expressed in terms of molar ratio of the oxides:

$1.05Na_2O \cdot Al_2O_3 \cdot 23.3SiO_2$

Similarly to the procedure as described in Example 1, MCB was subjected to the liquid phase chlorination using 1.0 gr. of the above-prepared Na ion-exchanged ZSM-5 zeolite as a catalyst either in the presence or absence of tetra-n-butyl ammonium bromide. After 3 hours of the chlorine gas blowing, the results shown in Table 4 were obtained.

TABLE 4

| | Comparative Examples | |
|---|---|---|
| | 4 | 5 |
| Quanternary ammonium salt | tetra-n-butyl ammonium bromide | — |
| Amount[1] (grs./gr. zeolite) | $1.8 \times 10^{-4}$ | — |
| MCB Conversion (%) | 17.4 | 52.0 |
| Selectivity (%) | | |
| PDCB | 76.5 | 79.3 |
| ODCB[2] | 21.5 | 17.8 |
| Others[3] | 2.0 | 2.9 |

[1]expressed as the weight of nitrogen atoms per unit weight of the zeolite
[2]ODCB: ortho-dichlorobenzene
[3]Others: including meta-dichlorobenzene and trichlorobenzene isomers

EXAMPLE 11

The chlorination procedure described in Example 1 was repeated except that 40 grs. of toluene was employed in place of the MCB. After 3 hours of the chlorine gas blowing, a toluene conversion of 53.3% and a parachloro-toluene selectivity of 67.5% were found to have been obtained.

COMPARATIVE EXAMPLE 6

The toluene chlorination procedure described in Example 11 was repeated except that the benzyl trimethyl ammonium chloride was omitted. After 3 hours of the chlorine gas blowing, a toluene conversion of 54.6% and a parachlorotoluene selectivity of 62.4% were found to have been obtained.

What is claimed is:

1. A process for preparing para-substituted halogenated benzene derivatives comprising subjecting a benzene derivative to halogenation by reacting the bezene derivative with elementary halogen in the liquid phase in the presence of a catalyst comprising a zeolite possessing the main pores which have the opening formed of a 12-membered oxygen ring;
wherein at least one quaternary ammonium salt is present in the reaction system.

2. A process as claimed in claim 1 wherein said quaternary ammonium salt is selected from compounds comprising a quaternary ammonium ion represented by any one of the following general formulae (I), (II) and (III):

wherein $R_1$, $R_2$, $R_3$ and $R_4$, which may be the same or different, each represent a hydrocarbonaceous group having from 1 to 20 carbon atoms and optionally containing carbon-to-carbon unsaturation or an aryl, hydroxyl, halogeno, ester or carboxyl group or groups;

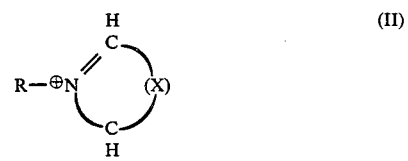

wherein R represents a hydrocarbonaceous group having from 1 to 20 carbon atoms and optionally containing carbon-to-carbon unsaturation or an aryl, hydroxyl, halogeno, ester or carboxyl group or groups, and X represents a $C_1$–$C_{11}$ hydrocarbon chain containing from 0 to 3 nitrogen atoms; and

wherein $R_1$ and $R_2$, which may be the same or different, each represent a hydrocarbonaceous group having from 1 to 20 carbon atoms and optionally containing carbon-to-carbon unsaturation or an aryl, hydroxyl, halogeno, ester or carboxyl group or groups, and Y represents a $C_3$–Chd 13 hydrocarbon chain containing from 0 to 3 nitrogen atoms.

3. A process as claimed in claim 2 wherein said quaternary ammonium ion is selected from the group consisting of alkyl-containing quaternary ammonium ions, aryl and alkyl-containing quaternary ammonium ions, aralkyl and alkyl-containing quaternary ammonium ions, quaternary ammonium ions containing a hydrocarbonaceous group substituted with hydroxy, halogen or ester group, pyridinium ions, quinolinium ions, imidazolinium ions, pyrrolidium ions, piperidinium ions and piperazinium ions.

4. A process as claimed in claim 2 wherein said quaternary ammonium ion is selected from the group consisting of tetramethyl-, tetraethyl-, tetra-n-propyl-, tetra-n-butyl-, phenyl trimethyl-, benzyl trimethyl-, 2-hydroxyethyl trimethyl-, 2-chloroethyl trimethyl- and 2-acetoxyethyl trimethyl-ammonium ions; methyl-, ethyl- and lauryl-pyridinium ions; methyl- and ethyl-quinolinium ions; 1,3-dimethyl imidazolinium ion; N,N-dimethyl pyrrolidinium ion; N,N-dimethyl piperidinium ion; and N,N,N'N'-tetramethyl piperazinium ion.

5. A process as claimed in claim 1 wherein said quaternary ammonium salt is used in an amount of $1 \times 10^{-5}$ to 0.1 gr./gr. of said zeolite, as calculated in terms of the weight of the nitrogen atoms contained in the molecular of said quaternary ammonium salt.

6. A process as claimed in claim 5 wherein said amount ranges from $1 \times 10^{-4}$ to $5 \times 10^{-2}$ grs./gr. of said zeolite.

7. A process as claimed in claim 1 wherein said starting benzene derivative is selected from the group consisting of benzene, monohalogenated benzenes and monoalkyl benzenes in which the alkyl group contains 1 to 10 carbon atoms.

8. A process as claimed in claim 7 wherein said starting benzene derivative is selected from the group consisting of benzene, monofluorobenzene, monochlorobenzene, monoiodobenzene toluene and ethylbenzene.

9. A process as claimed in claim 1 wherein said zeolite is selected from the group consisting of faujasite-type zeolites, zeolite L, mordenite, cancrinite, gmelinite and offretite.

10. A process as claimed in claim 9 wherein said zeolite is selected from the group consisting of zeolites Y and L.

11. A process as claimed in claim 9 wherein said zeolite is cation-exchanged and is modified with a salt of a metal selected from alkali, alkaline earth and rare earth metals in an amount of 0.1-90% by weight on the basis of the weight of said zeolite.

12. A process as claimed in claim 1 wherein said liquid phase halogenation is effected either batch-wisely or semibatch-wisely in the presence of 0.001-1 kgr. of said catalyst per liter of the reaction mixture and $1 \times 10^{-5}$ to 0.1 gr. of said quaternary ammonium salt per gr. of said zeolite, as calculated in terms of the weight of the nitrogen atoms, at a temperature of 0°-200° C. and at a pressure sufficient to maintain the reaction mixture in the liquid phase, while feeding a halogenating agent at a rate 1-1500 mols per kgr. of catalyst per hour.

13. A process as claimed in claim 1 wherein said liquid phase halogenation is effected in a continuous fashion in the presence of 0.001-1 kgr. of said catalyst per liter of the reaction mixture and $1 \times 10^{-5}$ to 0.1 gr. of said quaternary ammonium salt per gr. of said zeolite, as calculated in terms of the weight of the nitrogen atoms, at a temperature of 0°-200° C. and at a pressure sufficient to maintain the reaction mixture in the liquid phase, while feeding said starting benzene derivative at a rate of 0.5-300 ls. per kgr. of said catalyst per hour and a halogenating agent at a rate of 1-1500 mols per kgr. of catalyst per hour.

* * * * *